(12) United States Patent
Huang et al.

(10) Patent No.: US 11,179,083 B2
(45) Date of Patent: Nov. 23, 2021

(54) PHYSIOLOGICAL FLUID COLLECTION BAG WITH INSTANT DATA TRANSMISSION

(71) Applicants: Liji Huang, Santa Clara, CA (US); Chih-Chang Chen, Cupertino, CA (US)

(72) Inventors: Liji Huang, Santa Clara, CA (US); Chih-Chang Chen, Cupertino, CA (US)

(73) Assignee: Siargs Ltd., Santa Clara, CA (US)

( * ) Notice: Subject to any disclaimer, the term of this patent is extended or adjusted under 35 U.S.C. 154(b) by 414 days.

(21) Appl. No.: 16/202,407

(22) Filed: Nov. 28, 2018

(65) Prior Publication Data

US 2020/0163608 A1 May 28, 2020

(51) Int. Cl.
*B65D 81/00* (2006.01)
*A61B 5/20* (2006.01)
*A61B 5/145* (2006.01)
*A61B 5/00* (2006.01)

(52) U.S. Cl.
CPC .............. *A61B 5/208* (2013.01); *A61B 5/002* (2013.01); *A61B 5/14539* (2013.01); *A61B 5/201* (2013.01); *A61B 5/742* (2013.01); *A61B 5/7475* (2013.01); *A61B 2560/0228* (2013.01); *A61B 2562/028* (2013.01); *A61B 2562/0271* (2013.01); *A61B 2562/182* (2013.01)

(58) Field of Classification Search
CPC ......... A61B 5/208; A61B 5/201; A61B 5/207; A61B 5/14539; A61B 5/7475; A61B 5/742; A61B 5/0002; A61B 2562/182; A61B 2562/028; A61B 2562/0271; A61B 2560/0228; A61B 5/20; A61B 5/0022; A61B 5/002
See application file for complete search history.

(56) References Cited

U.S. PATENT DOCUMENTS

| | | | | |
|---|---|---|---|---|
| 5,769,087 | A * | 6/1998 | Westphal | A61B 5/14507 600/573 |
| 2010/0286559 | A1 * | 11/2010 | Paz | G01N 33/493 600/581 |
| 2011/0046514 | A1 * | 2/2011 | Greenwald | G01F 1/662 600/573 |
| 2016/0051176 | A1 * | 2/2016 | Ramos | A61B 5/208 600/573 |
| 2016/0051177 | A1 * | 2/2016 | Chen | A61B 10/007 600/573 |
| 2017/0097252 | A1 * | 4/2017 | Huang | G01F 1/692 |

(Continued)

*Primary Examiner* — Andrey Shostak (57) ABSTRACT

The design and structure of a physiological fluid collection bag with instant data transmission capabilities, utilizing a micromachined thermal time-of-flight flow sensor as well as integrated pH and calorimetric mass flow sensors for simultaneous and continuous measurement of the instant volumetric flow rate, accumulated total volume, pH and density of data of a collected fluid is disclosed in embodiments. The fluid collection bag includes a collection chamber and storage chamber wherein the sensors are installed inside the storage chamber of the bag and the bag is fully disposable. The fluid collection bag is able to measure the flow rate and instantly relay the data to a reusable data processing unit that can transmit the data to a designated data center or to medical staff.

8 Claims, 6 Drawing Sheets

(56) References Cited

U.S. PATENT DOCUMENTS

2017/0100068 A1\* 4/2017 Kostov .................. A61B 5/208
2019/0343445 A1\* 11/2019 Burnett ............. A61M 25/0017
2019/0365306 A1\* 12/2019 Laing .................. G01F 25/0007
2019/0365308 A1\* 12/2019 Laing ...................... G06F 9/542

\* cited by examiner

PHYSIOLOGICAL FLUID COLLECTION BAG WITH INSTANT DATA TRANSMISSION

BACKGROUND OF THE INVENTION

1. Field of the Invention

This invention generally relates to fluid flow measurement, and it particularly relates to instant measurement of physiological fluid with a fluid collecting container and disposable sensing elements. This invention is further related to in situ diagnosis devices and is additionally related to micro-machined thermal sensors or Micro Electro Mechanical Systems (MEMS) thermal flow sensing technology.

2. Description of the Related Art

Physiological bags are frequently used in medical applications for collecting the discharge physiological fluids and then estimate or measure the volume collected in the bags. In an intensive care unit, the water and electrolyte balance is a very important parameter for the patient. Before 1990s, most of such physiological fluid collection was done manually via a plastic bag and a scale to weight the amount collected and then converted the weight to the volume. Later, the measurement of the discharged liquid no longer require a separate measurement (see the disclosure example of U.S. Pat. No 4,743.236, Combination urine meter and urinary drainage bag and the method of use, May 10, 1988). The volume was directly read from the volume scales printed on the plastic bags. Although the scales of the predetermined volumes marked on the plastic collection bag eliminated the additional weight equipment, but the shape of the plastic bags may be inevitably leading to large errors. The improvements thereafter (U.S. Pat. No. 4,305.405, Urine meter bag, Dec. 15, 1981) changed the construction materials of the bag from soft plastics to hard plastics. The collection bag was also configured into dual hard bags. The dual bag configuration is similar to those principle used in a utility gas meter. One of the bags was used as the calibration utensil while the second one for collection such that accuracy of measurement can be further improved. Also the positions of the drainage valves were improved (U.S. Pat. No. 8,328,734. Urine meter with improved drain construction, Dec. 11, 2012) such that the measurement of the volume of the discharge liquid would be more accurate and the sample of the liquid can be easily accessed. However, use of the scale bags, the discharge fluid data are only collected manually at a set time and the values are totalized as the amount of the discharge by the patient each time is unavailable. In addition, parameters such as pH values, fluid densities are also important for the best of current practices; such data cannot be collected for the each discharge but can be done by averaged ones for unknown discharge times.

Use of an electrical flow meter to measure the urine flow (U.S. Pat. No. 4,051,431, Apparatus for measuring rate of urine flow electrically, Sep. 27,1977) was disclosed by streaming the urine into capacitor plates. It was supposedly relieved the manual measurement inaccuracy and labor time. However it was found not to be medically safe as there was a direct contact of the electrical current with the urine at measurement, which could have a chance to be channeled back to patient and also had potential to alter the urine chemical properties. Automatic measurement of the discharge physiological fluids by optical approach was disclosed by Jespersen (U.S. Pat. No. 4,343,316, Electronic urine flow monitor, Aug. 10, 1982) and by LeVeens (U.S. Pat. No. 4,532,936, Automatic urine flow meter, Aug. 6, 1985). In the disclosure by Jespersen, a pair of electronic valves were applied to control the urine flowing into a specific column and an optical sensor was used to monitor the fluid in the column; and in the disclosure by LeVeens a peristaltic pump with one set of pumping rates was used to empty a measurement column that was monitored by an optical sensor to determine whether the column was emptied. As the discharge physiological fluid such as urine could be in a very small volume or in the microfluidic regime, the proposed methodology accuracy will be incurred by the column volume which could be quite large compared to the total discharged volume. In addition, the approach will require a complicated setup with fixed devices to the collection pathway as well as the electrical power supply to the system; it would be then very impractical for many of the targeted applications where flexibility and disposability are very much desired. An improvement to the optical measurement was disclosed by Paz and Jacob (U.S. Pat. No. 6,640,640, Droplet counter for low flow rate, Nov. 4, 2003). The liquid flow rate measurement was achieved by counting the droplets formed from the fluid collected via two separate chambers. The upper chamber collected the fluid and channeled the fluid to a droplet generator that was housed at the inlet of the lower collection chamber. The optical sensor was used to count the droplets and then transform the number of droplets into the volume of the fluid. It solved the problem of low flow rate measurement but as the droplet size could not be precisely controlled, the measurement would then have a large error that is not desired. In addition, the complete system requires the fixed sensor and system that would be bulky and could only be applied in predetermined places. Furthermore, the droplet formation was via a large flow resistance droplet generator and the fluid drainage required the natural gravity; it would be difficult to measure the fluid that would not have the required mass to pass through the droplet generator.

A disposable measurement approach of the fluid volume for the fluid collection bag was disclosed by Boiarski (U.S. Pat. No. 7,892,217, Variable cross-section containment structure liquid measurement device, Feb. 22, 2011; U.S. Pat. No. 8,424,376, Container for physiological fluid, Apr. 23, 2013). This disclosure preposed the printed resistors from the bottom to the top on the collection bag where the resistance will be altered by the added liquid. Hence the change of the resistance due to the presence of fluid in the collection bag can be used to measure the level of the fluid inside the collection bag which is further converted into the liquid volume. As the printed resistors will be very cost effective, the physiological fluid collection bag can then be fully disposable. However, such a level measurement is based on the assumption that there will be no deformation of the fluid collection bag. This could be not practical as the disposable fluid collection bags are mostly made of soft plastic which is easy to be deformed and make the level measurement to correspond the volume of the fluid inside the collection bag difficult. Furthermore, to get the instant measurement of the discharged fluid of the collection bag will need a resistance data acquisition equipment. Therefore the desired portability or mobility of the collection bag would not be feasible.

SUMMARY OF THE INVENTION

It is therefore the object of the present disclosure to provide a design and configuration of the physiological collection bags that can provide accurate and instant measurement of the volumetric value for the fluid discharged from the patient. It is desired for the fluid collection bag that can also measure the instant pH value and the density of the fluid. The fluid collection bag can further transmit the instant measuring dam of the discharged or excretory fluid volume, and as well as the pH value the fluid density to the relevant parties such that the critical data (e.g. electrolyte balance) from the patient's discharge fluids can be timely identified and thus proper medical procedures can be exercised. The fluid collection bag shall be stand-alone without the requirements to be wire-connected externally for data acquisition and transmission whereas the collected data acquired can be directly transmitted wirelessly to the doctor's data center or to a nearby stationed data processing device or via a smart device to be further relayed to the patient attention control center or medical data center for additional data process and distributing to the relevant parties. The desired fluid collection bag shall also be fully disposable from preventing cross-contamination and medical hazard processing. For different purposes of disposability, the fluid collection bag shall also be opted for having only the necessary parts enclosed inside the disposable bag; wherein the electronics for data acquisition and data transmission can be assembled into a separate non-disposable or reusable package that can be connected to the disposable bag via a data cable.

In one preferred embodiment, the disclosed digital physiological collection bags shall use the micro-machined thermal time-of-flight flow sensor to directly and instantly metering the discharge fluid. The flow sensor shall also integrated with a pH sensor and a density sensor to instantly register the key parameters of the discharge fluid. The conventional physiological collection bags are normally made with soft or hard plastics with scales on the bags. The data are collected by the medical staffs via visual estimation and since the collection data are set periodically, which are depending on the patient's status, it is not possible to have the data registered instantly and most likely the readings will be from multiple discharges. Hence, it would not be possible to register the critical parameters from live discharge fluid, in particular the change of these parameters. For example, the renal perfusion which is an indication of glomerular filtration rate (GFR) and directly related to the kidney*function will be very much related to the urine flow status. In addition, for the urine monitor and analysis, the present practice is to sample the fluid from the urine bag and then sent to the designated laboratory for analysis. However, as the sample frequency is mostly one or two times a day, the data shall not be able to reflect the changes of the patent's urine status but from multiple discharged urine mixture. The instant monitoring of these parameters therefore not only could reveal the patient's status quo and shall assist the evaluation and proper medication to the patient by the doctors. It shall also significantly reduce the medical staff's workload.

In another preferred embodiment, the disclosed digital physiological collection bags with the micro-machined sensing elements shall have an extended measurement dynamic range. For the current available liquid flow meters, measurement at a wide dynamic range with a media compatible and a cost effective formality is not available due to the low flow rate of the glomerular filtration. However in order to accurately metering the instant urine flow discharged from the patient, the meter needs to have a wider dynamic range to capture all possible occurrences. The present disclosure senses the fluid flow by utilizing a plural pairs of sensing elements that are symmetrically or asymmetrically placed on the micro-machined sensor chip. Each pair of the sensing elements shall cover the designated flow range where the normal glomerular filtration rates are about 120~170 mL/min. With this design, the dynamic range of the present disclosure is substantially larger than those required for the applications.

In another preferred embodiment, the disclosed digital physiological collection bags with the micro-machined sensing elements shall have the sensing elements made in the form of a combined set of a flow sensor chip, a pH sensor chip and a density sensor chip that are placed in the middle of a channel in the collection bag. In order to metering and registered the discharged fluid accurately, it is desired that the sensing elements shall be placed in a designated flow channel that will have a diameter in millimeter dimension. This is to ensure the discharged fluid can be collected and metered in a defined channel. In the present disclosure, the micro-machined sensing elements are made on a millimeter dimension silicon or a glass substrate with a thermal isolation cavity for better response and performance. The sensing elements are further disposed on a localized membrane on the silicon substrate with a submillimeter dimension, which can define the minimal channel size. In all cases, the present disclosure has a flow conditioner placed at the flow channel entrance to ensure the fluid flow stability. The flow conditioner also serves as an air bubble remover such that the fluid sensing will not be altered from the original calibration.

In another preferred embodiment, the disclosed digital physiological collection bags with micro-machined sensing elements for instantly metering the discharged fluid shall utilize the thermal time-of-flight flow sensing measurement principle. To achieve the desired performance, the desired thermal time-of-flight flow sensing elements shall be capable of acquiring multiple parameters from the flow fluids. For measurement of the fluid flow rate or in the case of a urine collection, and the glomerular filtration rate through the designated or defined fluid flow channel, it is desired in the present disclosure to drive the sensing elements with alternative current such that no deposition on the sensing element surface to alternate the continuous metering. The time-of-flight is less sensitive to the flow instability and interferences of other factors such as fluid properties and in particular it is more sensitive to the lower flow rate responses. The additional pair of calorimetric sensing and thermal dissipative sensing elements integrated on the same micro-machined sensor chip shall be able to directly acquire the mass flow rate data and further relate to the fluid mass flow rate and fluid thermal and/or concentration properties for the discharged fluid.

In another preferred embodiment, the disclosed digital physiological collection bags with the micro-machined sensing elements shall have the pH sensor and the density sensor. The pH sensor is preferred made with the solid state sensing principle that can be further micro-machined on a glass substrate. For the prevention of the pH value drift or deviation due to tire environmental effects, a thin film solid reference electrode shall also be included in the same sensing chip. The density sensor shall be made by using the micro-machined cantilever that shall metering the density from the vibrational frequency changes based on a pre-calibrated procedure. The density of the discharged fluid may require a high precision and the variation of the density is often in a minimal and small range. Therefore additional parameters shall be collected for further comparison to obtain a precise measurement. These parameters shall include the thermal conductivity and thermal diffusivity variations due to the different densities of fluids.

In another preferred embodiment, the disclosed digital physiological collection bags with the micro-machined sensing elements shall be in the form of disposable where only the necessary components being constituent of disposable units and those components such as the control electronics and cables will be reusable. For the best performance, the collection bag shall be divided into two connected units where one unit preferably at the top of the collection bag shall serve the purpose of a fluid collection chamber such that the discharged fluid shall not have a discontinuous flow character before it reaches to the volume measurement sensing elements, which shall be detrimental for the accurate measurement. The other unit shall be serving as the fluid retaining chamber and is preferably placed at the bottom of the collection bag where all of the discharged fluid shall be retained. The collection chamber can be in the form of a triangle reversely formed with respect to the collection bag top where the lowest portion shall be connected to the designated flow channel where the fluid volume, fluid pH value and fluid density shall be measured.

In another preferred embodiment, the disclosed digital physiological collection bags with the micro-machined sensing elements shall have the measurement unit installed inside the flow channel and the measurement unit shall contain three micro-machined sensors for fluid volume, pH values and fluid density. The measurement unit shall be preferably placed at the middle of the flow channel such that flow stability can be best maintained. It is further preferable for the purpose of disposability that the control electronics shall be separated from the measurement unit and connected to the measurement unit with a medical grade cable for data transmission. The control electronics shall contain the data processing and data relay functions to the designated data center for instant reach to the medical doctor or staff. It is preferable that the data shall be transmitted from the control electronics to the data center via a cable network in order to prevent the possible interference in a medical environmental, although various wireless data transmission protocols such as BLUETOOTH, ZIGBEE, and mobile network data shall also be preferred if the environment allows.

In yet another preferred embodiment, the disclosed digital physiological collection bags with the micro-machined sensing elements shall have a check valve installed at the top of the collection bag. Such a valve shall connect the physiological fluid source and the collection bag, which shall prevent the fluid from filling back the tube to the fluid source. Another sample valve shall be installed at the bottom of the collection bag such that the fluid sample can be obtained in case a detailed analysis shall be required.

The present disclosure provides a new concept and a new design of a digital physiological collection bag with the micro-machined sensing elements for instant discharged fluid volume, pH values and densities. In the case of urine discharge, such data for glomerular filtration rate, indication of acute renal failure could also be obtained. It substantiates it from the conventional manual visual estimation of the multiple discharged fluids with instant data transmission of each discharge that can provide instant critical data for the patient under monitor. The disclosure in particular can provide automatic and continuous monitor of the critical parameters for the discharge fluid without the needs of a medical staff attention which consequently substantially boosts the medical data accuracy and effectiveness, while it also reduced significantly the labor cost. These and other objectives of the present disclosure shall become readily apparent upon further review of the following drawings and specifications. And additionally for those with the knowledge of the art, the digital physiological fluid collection bag could be further utilized for detailed instant analysis with addition of sensors that shall be deemed necessary that would be the ultimate goals for the instant and automated medical data.

DETAILED DESCRIPTION OF THE PREFERRED EMBODIMENTS

Figure 1:
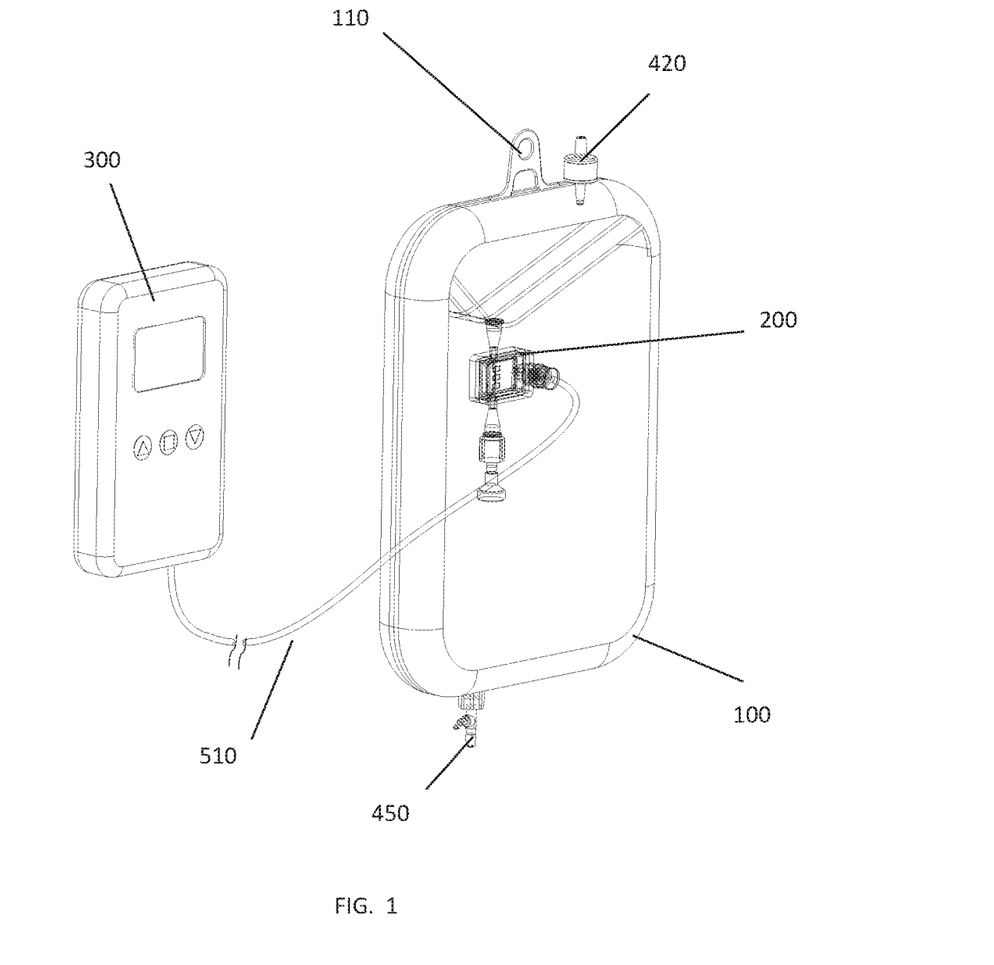
FIG. 1 is the digital physiological fluid collection bag assembly showing the bag configuration with a fluid collection chamber and a fluid retaining chamber where the measurement unit is installed. The bag shall be fully disposable while the control electronics that is connected to the bag via a medical grade cable. The control electronics shall process the measured data and then instantly transmit such data to the designated data center that can be reached by the doctor or medical staff.

For the preferred embodiment, the present disclosure of a new digital physiological fluid collection bag that utilizes the micro-machined integrated thermal time-of-flight flow sensor for instant volume and pH sensor and density sensor for instant fluid analysis is show in FIG. 1. The new concept for a physiological fluid collection has two crucial improvements over the current visual data assessment from a plastic bag. On the one hand, the capability of instant and digital data streaming for the high precision measurement of the actual discharged fluid volume enables the knowledge of the patient's instant and continuous status under medication which is not possible with the current technology. The constant feedback of the patient's status enables the medical doctor to precisely make decisions on the care plan for the particular patient that not only significantly boosts the recovery but also may save significant medical resources. In the example of urine collection, the patient's glomerular filtration rate, electrolyte balance, and acute renal failure could all be instantly become available to the medical doctor. On the other hand, the addition of the fluid analytical sensors such as pH sensor and density sensor that are disclosed in the present invention also allows the data to often be obtained by sampling and laboratory time at future. This addition also allows the patient's physical status to be plotted in real time that could be crucial in particular for patient having kidney related diseases. It is also easily extended to the additional variety of the fluid collection bags with other new chemical and or physical data analysis sensors, which should be a desirable function. The present concept and design therefore discloses a new physiological fluid collection bag that can use the micro-machined physical and chemical sensors to instantly measure the desired data of the fluid and instantly transmit such data to the medical doctor or staff, which can significantly help the recovery of the patient with more precise knowledge and feedbacks from the instant status of the patient through a much better, timely and appropriate care plan.

The digital physiological fluid collection bag shown in FIG. 1 shall be constituent with two main parts, the physiological fluid collecting and metrology unit 100 which has the physical bag made of medical grade plastics for collecting the fluid wherein the metrology data sensing module 200 measures and digitizes the physical volume of the collected fluid. This pan shall be fully disposable or for one-time usage only, and it shall be preferably connected via a shield cable 510 to the data analysis. And processing unit 300 shall have the functionality for data processing, analysis, as well as for further data transmission.

Figure 2:
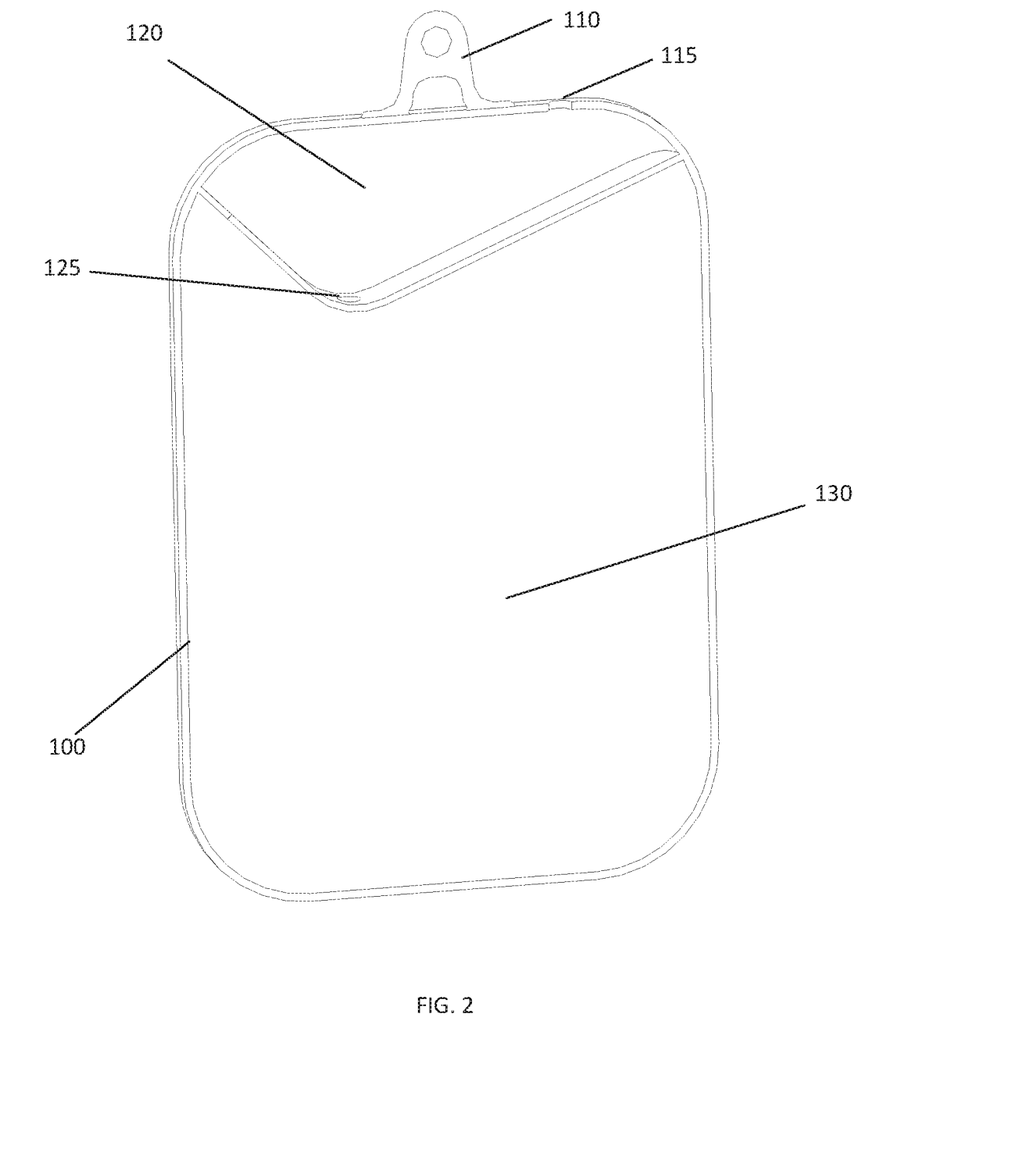
FIG. 2 is a detailed view of the configuration of the two chambers inside the digital physiological fluid collection bag where the upper chamber is used for collect the fluid such that the discontinuation of the discharge can be eliminated while the lower chamber is used for the detainment of all discharged fluid.

For the preferred embodiment, the digital physiological fluid collection bag will have two chambers as shown in FIG. 2. The upper chamber 120 shall be used for guiding the physiological fluid into the fluid release channel 125. For accurate measurement with a fluid flow sensor, it is critical to have a channel completely filled with the fluid to be measured. Therefore a channel entrance shall be at the very bottom of the upper chamber 120, leading to the channel with which the fluid collected shall be populated. The second chamber 130 shall then be used for the fluid storage after the fluid is measured. In order to prevent the fluids from filling back to the patient, at the entrance 115 on the bag for the incoming fluid, a check valve 420 is installed such that no fluid after entering into the bag shall be able to escape. From time to time, it is desired to have the collected fluid to be further analyzed by a medical laboratory. To this purpose, a manual valve 450 shall be placed at the bottom of the bag, with which the sample of the fluid shall be easily accessed with an external utensil or a medical fluidic sample holder. Another feature for the physiological fluid collection bag is a fixture 110 that shall be applied to a hook or similar structure such that the collection bag will be kept in a relatively still status, which shall also be helpful for the performance of the metrology module 200.

Figure 3:
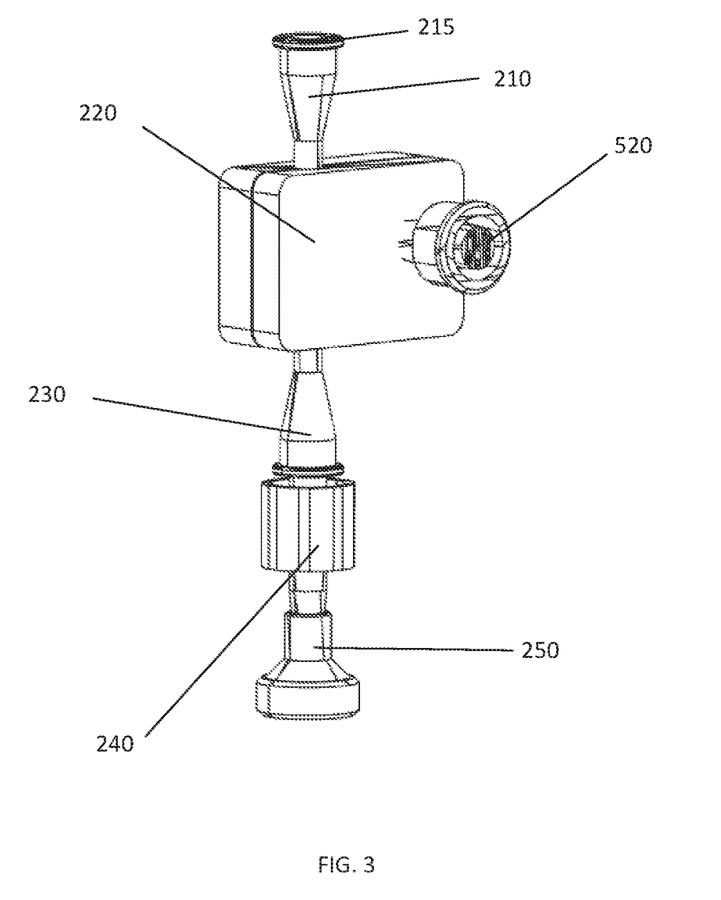
FIG. 3 is the detailed disclosure of the measurement unit with the flow stabilizing channel. The chamber is embedded with three sensing elements for fluid volume, pH values and densities.

FIG. 3 exhibits the detailed structure and configuration of the metrology data sensing module 200. This module shall be the key component of the digital physiological fluid collection bag. The fluid entrance collector 210 is a short connection fluidic channel with its channel size reduced towards the entrance of the metrology unit 220. On the top of the fluid entrance collector 210, a click fasten ring 215 is used to connect with tight seal to the fluid collection chamber 120 of the fluidic collection bag. This configuration of the collector 210 with a reduced fluidic flow channel shall forces the incoming fluid running with a reduced flow rate that shall also help the reduction of bubbles inside the fluid wherein a filled channel would be better ensured. The ratio of the entrance channel size to that for the connection with the metrology unit in the preferred embodiment shall be 2:1 to 5:1 depending on the fluidic collection bag size. A bubble filter could also be installed at the entrance 215 assisting the clearance of the possible bubbles which shall be detrimental for an accurate measurement of the fluidic volume. The exit channel 230 has a similar shape as the fluid entrance collector 210 but with a larger channel size section placed towards the fluid exit direction such that it shall have a faster release to the fluid storage chamber 130. The buffer container 240 shall be used for assisting the removal of bubbles as well as for reducing the traveling speed of the fluid such that the accuracy of the measurement can be ensured. In a preferred embodiment, a pressure sensor can also be placed at the bottom towards the exit of the fluid from the measurement channel and the sensor can be used for additional information of the fluid volume passing through the channel. The unit 250 after the buffer 240 is used for guiding the fluid into the storage chamber 130, and finally the complete module shall be connected preferably by a medical grade connector 520 via an electrically shielded cable 510 to the data process unit 300.

Figure 4:
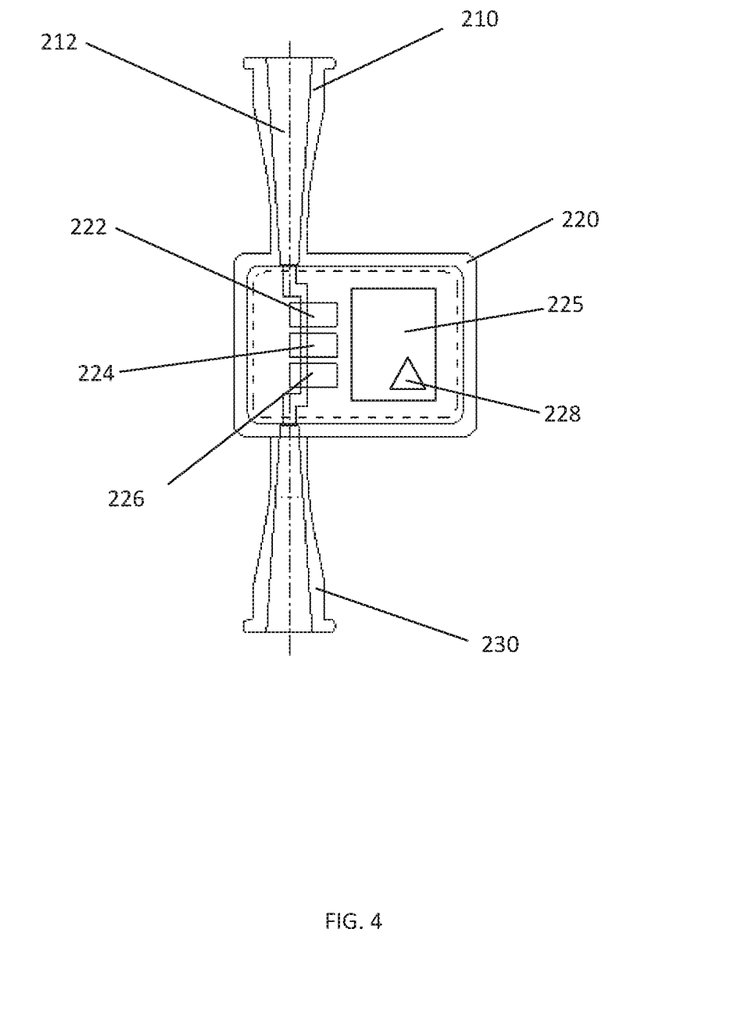
FIG. 4 is the cross section revealing the arrangement of the three sensing elements and one calibration data storage unit with the interface for connection to the control electronics.

The detailed illustration of the metrology data sensing module 200 can be found in FIG. 4 which is a cross-section of the main portion of that shown in FIG. 3. The fluid flow channel 212 has a diameter gradually reduced from a fluid entrance to before reaching a measurement channel wherein three sensors are installed: 222 is a pH sensor that in the preferred embodiment is made via a micromachining process, and this sensor shall measure the pH value of the collected fluid; 224 is preferred to be a MEMS thermal time-of-flight flow sensor that can motoring measure the volume of the collected fluid; and 226 is a density sensor that shall be in the preferred embodiment also made with a micromachining process. The sensors are connected directly to a printed circuitry board (PCB) 225 on which the connector 228 shall be connected externally to the medical grade connector 520. The construction materials of the module shall be completed with medical grade plastics in which the chambers of the sensing unit 220 shall be hermetically sealed and shall be water or fluid proof including the interface of the connector 228. In a preferred embodiment, and for the purpose of disposability, the electronics on the PCB shall be limited to only an EEPROM in which the calibration data for each of three sensors shall be stored, as even with a fully automatic assembly process, there would be some minor deviations for each of the installed MEMS sensors, and the data in the EEPROM will eliminate such deviations via the calibration of each of the three sensors. Such deviations include, for example, offset, full scale, and output linearity.

For the preferred embodiments, the pH sensor shall provide continuously measurement for the pH values of the collected fluid. For the concerns of a human fluid, such as urine, the pH sensor shall only need to cover a relatively narrow range but a high resolution and accuracy shall be required. The preferred pH values to be measured shall be close to 6.2 with a span no more than ±2.5. As the abnormal pH value of urine, for example, could be an indication of certain diseases such as acidosis or dehydration for low pH values or urinary tract obstruction or salicylate intoxication for high pH values. As the accurate measurement of the pH values often requires a fresh sample, the in situ continuous measurement by the embedded pH sensor would provide the most valuable pH data for the patient, which often could not be performed by the current practice because the sampling time is often depending on the schedule of the medical staff on shift and the availability of nearest laboratory. Also the continuous pH data plot shall reflect any medical condition improvement of the patient with time, which is also not be possible with the current technologies.

For the preferred embodiment, the MEMS thermal time-of-flight (TTOF) flow sensor shall provide continuous metering on the volume of the discharge fluids, and shall record the start and stop for each discharge. In the current practice, for example, for urine discharge, the urine collected by the urine bag cannot record any information of amount, timing and actual flow information as for the collected urine.

The urine may be from one time or may be from multiple time discharges at the time the medical staff inspects the physical urine bag. In this particular example, the urine flow shall be an indication of renal perfusion, or an indication of Glomerular Filtration Rate (GFR), changes in extracellular fluid and kidney function. In an intensive Care Unit (ICU), the infused fluids to a patient is well documented, but the precise discharge information from the patient is missing, and hence some parameters such as instant changes in patient's electrolyte balance could not be made available. With the in situ TTOF flow sensor, not only the discharged fluid can be precisely measured by the volume but exactly by the volume of each discharge. In addition, the TTOF flow sensor shall also be able to instantly measure the flow rate of the discharged fluid. Such a flow rate would be a direct indication of GFR with which the possibility of a chronic renal failure or acute renal failure shall be captured instantly and timely. Hence, for this reason, the TTOF flow sensor shall be able to cover the flow range from low 100 mL/min to 200 mL/min or the average flow rate can be deducted from the volume and time of each complete discharge that is real time metered.

For the preferred embodiment, tire micromachined density sensor shall register the changes of tire discharge fluid in an instant and timely manner. The density or specific gravity that is associated to the osmolarity is a directly indication of wire impurities inside the discharged urine. A higher specific gravity than that of a normal value (1.003 to 1.035) is often a direct indication of urinary tract infection or some malfunction of kidney. The continuous data made available shall be very valuable in particular for monitoring the patient in recovering from a kidney disease or other related disease. Any abrupt changes with the instant data shall be able to provide direct warnings to the medical staff, and therefore an instant remedy could be timely applied.

Figure 5:
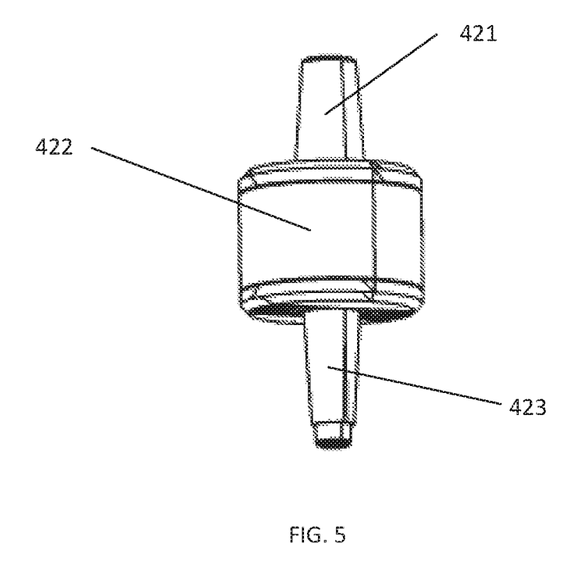
FIG. 5 is the schematic for a check valve.
Figure 6:
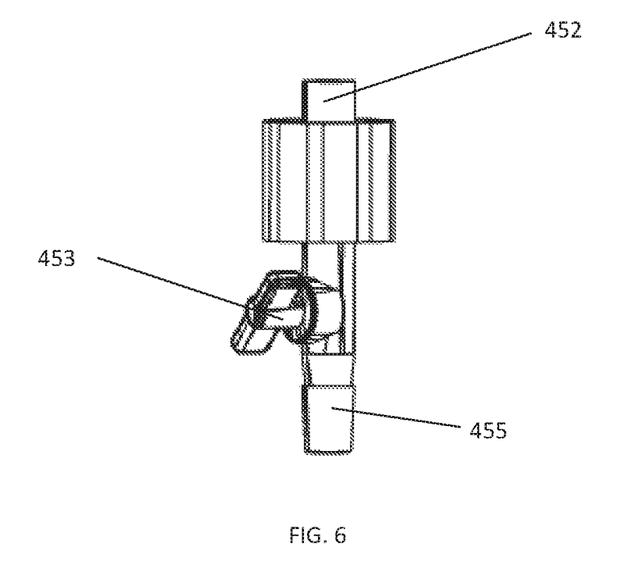
FIG. 6 is the schematic for a sample valve.

For the preferred embodiment, the check valve 420 (FIG. 5) shall have a v-nozzle 421 for connecting to a guided tube from a patient while another v-nozzle 423 directs the fluid into the fluid collection chamber 120. The valve element shall be placed inside the enclosure 422 to prevent the fluid back filling from the fluid collection chamber 120 to the patient via the guided tube, FIG. 6 is an illustration of the manual value 450 installed at the bottom of the digital physiological fluid collection bag. The tube 452 is connected to the fluid storage chamber of the bag while the pipe 455 shall direct the fluid to the sample utensil or sample container when the manual valve 453 is switched to open position.

Figure 7:
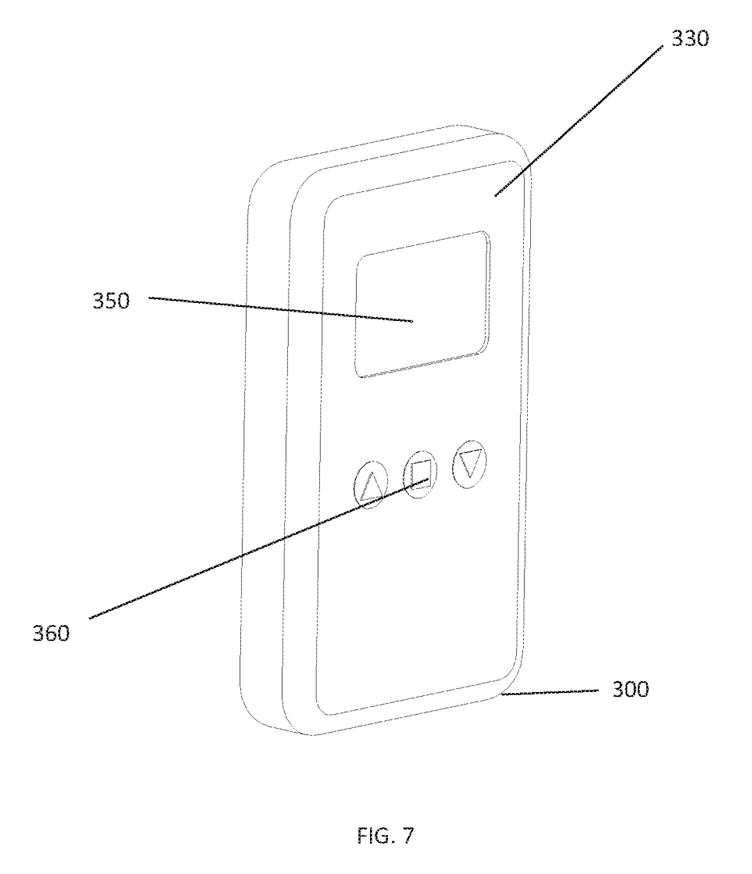
FIG. 7 is the block diagram of the control electronic unit.

For the preferred embodiment, the data processing unit 300 shall have a display 350 such as a liquid crystal display (LCD) or light emitting-diode (LED) or organic light emitting-diode (OLED). A keyboard 360 shall be used to program the data processing information or enter parameters or information of the patient. Inside the front cover 330, there are control electronics containing an analog to digital converter, a microprocessor for data processing, and a data storage unit. The data processing unit 300 shall further contain a wireless data transmission unit such as a low energy BLUETOOTH unit, an NB-IoT module or a LoRa module. In case that wireless data transmission is not preferred, wired data transmission via a local network using interfaces such as 10-Link or standard RS485 Modbus would be available. The data can be transmitted to a central station assigned by the medical staff or directly to the smart devices owned by specific medical staff.

For the additional preferred embodiment, the digital physiological fluid collection bag for those in the art could be further incorporated with additional features such as a color recognition sensor and other chemical sensors, and the data shall be available for use for full spectrum medical data analysis. It is readily and apparently that the applicable fluid shall preferably be urine but shall also be applicable to general purpose physiological fluid collections.

The invention claimed is:

1. A digital physiologic fluid collection bag with instant data transmission capabilities, able to instantly and continuously measure volume, pH, and density of a collected discharge fluid, the digital physiologic fluid collection bag comprising:
   two separate chambers wherein an upper chamber is used as a fluid collection chamber and a lower chamber is used as a fluid storage chamber;
   a "V" shaped structure configured to separate the fluid collection chamber and the fluid storage chamber, wherein an opening for fluid passage is disposed at the very bottom of the "V" shaped structure;
   a data sensing module arranged in the fluid storage chamber, comprising a guided fluid channel having a diameter that is gradually reduced from a fluid entrance end at the opening of the "V" shaped structure towards a fluid measurement sensing channel to decrease a chance for trapping air bubbles; the data sensing module further comprising a fluid sensing and measurement module, configured to measure a density of the discharge fluid, and having at least three sensing elements inside the fluid measurement sensing channel, wherein the at least three sensing elements comprise a Micro-Electro-Mechanical-System (MEMS) thermal time-of-flight flow sensor for motoring measuring volume flow of the discharge fluid; a pH sensor for measuring the pH of the discharge fluid, and a calorimetric mass flow sensor to measure a mass flow of the discharge fluid; wherein each of the sensors is connected to an enclosed and hermetically sealed printed circuit board (PCB) comprising individual calibration data for each sensor;
   a check valve which is configured to be connected between a guided tube from a patient and the fluid collection chamber to prevent the collected discharge fluid back filling to the patient; and
   a manual release valve at the bottom of the fluid storage chamber for sample extraction;
   wherein the fluid sensing and measurement module is configured to be connected, via a medical grade and electrically shielded cable, to a data processing, analyzing and transmission unit for data relay purposes, the data processing, analyzing and transmission unit used to process a measured data from the fluid sensing and measurement module and to transmit the measured data to a data center or a device accessible to medical staff;
   wherein the digital physiologic fluid collection bag is disposable.

2. The digital physiological fluid collection bag with instant data transmission capabilities of claim 1, wherein an angle for the "V" shaped structure is ranged from 70° to 140°.

3. The digital physiological fluid collection bag with instant data transmission capabilities of claim 1, wherein the guided fluid channel connects directly to the opening of the "V" shaped structure; wherein reduction of the channel diameter from largest to smallest is from 2:1 to 5:1 depending on a discharge fluid total volume or size of the fluid collection bag.

4. The digital physiological fluid collection bag with instant data transmission capabilities of claim 1, wherein the MEMS thermal time-of-flight flow sensor is used to measure instant volume and register total volume of each discharge; and wherein the MEMS thermal time-of-flight flow sensor takes data at least every one minute.

5. The digital physiological fluid collection bag with instant data transmission capabilities of claim 1, wherein the pH sensor is micromachined on a glass substrate, is able to measure a pH value from 4.0 to 8.0 with an accuracy better than ±0.5%, and takes data at least every one minute.

6. The digital physiological fluid collection bag with instant data transmission capabilities of claim 1, wherein the fluid sensing and measurement module has an electrically erasable programmable read-only memory (EEPROM) to store the individual calibration data; wherein the EEPROM is installed on the enclosed and hermetically sealed PCB and connected to the sensors such that the EEPROM and the sensors can be disposed after use; and wherein the PCB has a medical grade and hermetically sealed connector through which the medical grade and electrically shielded cable can be connected to relay data to the data processing, analyzing and transmission unit.

7. The digital physiological fluid collection bag with instant data transmission capabilities of claim 1, further comprising a fluid release channel after the fluid measurement sensing channel, the fluid release channel having a varied channel diameter, wherein a top channel end with a smallest diameter is connected to the fluid measurement sensing channel while a bottom channel end with a largest channel diameter is connected to a buffer container, wherein the buffer container directs the discharge fluid into the fluid storage chamber.

8. The digital physiological fluid collection bag with instant data transmission capabilities of claim 1, wherein the check valve is installed at a fluid entrance to the fluid collection chamber to prevent the collected discharge fluid back filling to the patient.

\* \* \* \* \*